(12) United States Patent
Scheiner et al.

(10) Patent No.: US 8,448,510 B2
(45) Date of Patent: May 28, 2013

(54) DEVICE FOR MONITORING THE LEVEL OF THE CONDENSATE COLLECTED IN THE MEASURING CYLINDER OF A STANDARDIZED DISTILLATION APPARATUS AND METHOD IMPLEMENTED BY USING THIS DEVICE

(75) Inventors: Herbert Scheiner, Grünsfeld (DE); Thomas Herold, Boxberg-Uiffingen (DE)

(73) Assignee: Instrumentation Scientifique de Laboratoire ISL, Verson (FR)

( * ) Notice: Subject to any disclaimer, the term of this patent is extended or adjusted under 35 U.S.C. 154(b) by 816 days.

(21) Appl. No.: 12/525,966

(22) PCT Filed: Feb. 8, 2008

(86) PCT No.: PCT/FR2008/050198
§ 371 (c)(1),
(2), (4) Date: Sep. 30, 2009

(87) PCT Pub. No.: WO2008/104689
PCT Pub. Date: Sep. 4, 2008

(65) Prior Publication Data
US 2010/0031743 A1 Feb. 11, 2010

(30) Foreign Application Priority Data
Feb. 13, 2007 (FR) .................................... 07 53232

(51) Int. Cl.
*G01F 23/00* (2006.01)
(52) U.S. Cl.
USPC ........................................ 73/293; 73/290 R

(58) Field of Classification Search
USPC ............................................... 73/290 R, 293
See application file for complete search history.

(56) References Cited

U.S. PATENT DOCUMENTS

| | | | |
|---|---|---|---|
| 3,364,731 | A | 1/1968 | Hook |
| 4,759,825 | A | 7/1988 | Medvey et al. |
| 5,053,111 | A | 10/1991 | Ellerbe, Jr. |
| 6,173,609 | B1 | 1/2001 | Modlin et al. |
| 2005/0213633 | A1 | 9/2005 | Burian et al. |

FOREIGN PATENT DOCUMENTS

| | | |
|---|---|---|
| DE | 3526644 A1 | 1/1987 |
| DE | 10354856 A1 | 7/2005 |
| WO | WO03/091667 A2 | 6/2003 |

OTHER PUBLICATIONS

English translation of the Written Opinion of the International Searching Authority related to International Application No. PCT/FR2008/050198.

*Primary Examiner* — Daniel Larkin
*Assistant Examiner* — Jamar Ray
(74) *Attorney, Agent, or Firm* — Faegre Baker Daniels LLP

(57) ABSTRACT

Device for monitoring the level of the condensate collected in the measurement cylinder of a standardized distillation apparatus for automatically distilling liquid specimens, characterized in that it comprises: on the one hand, a double optical barrier emitting a central beam centered on the measurement cylinder (1), so as to allow detection of the part below the meniscus, and an eccentric beam offset with respect to the central beam and located close to the wall of the measurement cylinder (1), so as to allow the part above the meniscus to be detected; and, on the other hand, a fixed optical barrier intended for counting the drops of condensate falling into the measurement cylinder (1) during distillation.

5 Claims, 2 Drawing Sheets

DEVICE FOR MONITORING THE LEVEL OF THE CONDENSATE COLLECTED IN THE MEASURING CYLINDER OF A STANDARDIZED DISTILLATION APPARATUS AND METHOD IMPLEMENTED BY USING THIS DEVICE

This application is a U.S. National Phase Patent Application based on International Application Serial No. PCT/FR2008/050198 filed Feb. 8, 2008, the disclosure of which is hereby explicitly incorporated by reference herein.

BACKGROUND OF THE INVENTION

1. Field of the Invention

The present invention relates to a device which allows monitoring of the level of the condensate collected in the measuring cylinder of an automatic standardized device for distillation of liquid samples, in particular samples of petroleum products under atmospheric pressure.

Such a distillation device allows the measurement of the distillation parameters of these samples to be carried out, while complying with a predefined test standard selected from a plurality of possible test standards.

2. Description of the Related Art

It is known that the distillation parameters of petroleum products are representative of the performance levels of these products and the risks which may be involved for those who use them.

The determination of these parameters is particularly significant in the case of fuels which are intended for the automotive industry or aviation where problems relating to safety are of prime importance.

These parameters are in particular tables or lines representing the percentage of a sample evaporated in accordance with the temperature during a distillation or the volume of the residue and the losses.

Specialists can deduce from these parameters the behaviour of a specific petroleum product in a specific situation and therefore determine whether or not this product can be safely used, in order to obtain the desired performance levels.

In this context, specialists have stipulated various test standards which define very precisely the conditions under which such distillation characteristics must be obtained.

Consequently, in order to provide usable results, the distillations must be implemented with these standards being strictly complied with.

Various automatic distillation devices are currently commercially available and allow the distillation parameters of a liquid sample to be measured, while complying with a predefined test standard.

These standardized distillation devices generally comprise:

a fixed frame, a heating chamber which comprises a heat-generating element, in particular a heating resistor, a series of distillation flasks which correspond, respectively, to at least one test standard and which are capable of being fixed to the frame of the device in a fixed position, the column of these flasks being able to be closed by means of a fluid-tight closure stopper which is provided with a thermometer allowing the temperature of the evaporated vapours to be measured and which comprises a lateral branch which is intended to be connected to a condensing tube, a series of insulating plates which are intended to be mounted above the heat-generating element in order to close the heating chamber at the upper portion thereof and which are each provided with a central opening having a geometry which is adapted to that of the base of an associated distillation flask, a measuring cylinder which allows the condensate to be collected and which is provided with means for measuring the quantity of condensate collected in this manner, and control and regulation means which allow an operating variable of the heat-generating element to be controlled and varied over time, in particular the temperature or the power of this element in order to obtain distillation parameters in accordance with a predefined test standard.

So that the distillation parameters of a sample obtained are completely representative of this sample, it is essential for the measuring means with which the measuring cylinder is provided to be capable of allowing very precise determination of the level of condensate collected in this cylinder and very precise monitoring of this level over time.

To this end, it has already been proposed to provide standardized distillation devices of the above-mentioned type with means for measuring the quantity of condensate collected in the measuring cylinder comprising an optical system which is constituted by a transmitter/receiver pair which is capable of transmitting an infrared beam which is directed horizontally through the measuring cylinder and co-operating with a linear driving action via a step motor which can be moved in vertical translation in order to allow this beam to be aligned with the meniscus of the condensate collected in this cylinder in order to allow the height of this meniscus to be detected.

In such distillation devices, the infrared beam may or may not be centered on the center axis of the measuring cylinder.

The linear driving by means of a step motor can be very precise in order to allow the infrared beam to be moved by a pitch in the order of 0.05 mm in the vertical plane.

Such measuring means which are based on transmitting and receiving an infrared beam further have the advantage of not being affected by ambient light.

However, it should be noted that an eccentric light beam, which passes between the center and the wall of the measuring cylinder, allows a clear distinction to be made between the liquid sample to be analyzed and the air located above this sample in so far as, when it is located below the level thereof, it is interrupted and can no longer reach the detector.

However, such an eccentric light beam does not allow it to be determined whether the location is below the lower portion of the meniscus, that is to say, the "true" meniscus, or between the lower portion and the upper portion thereof.

An eccentric light beam consequently only allows the upper portion of the meniscus to be detected so that, in order to obtain the "true" meniscus, it is necessary to carry out a correction which is dependent on the sample and is therefore imprecise.

A central light beam itself has the disadvantage of not allowing a sufficiently reliable level measurement to be obtained, in particular at the beginning of distillation where, taking into account phenomena of capillarity, the meniscus of the condensate is not completely constituted with the result that it is impossible to detect the lower portion thereof.

Furthermore, a center beam is not interrupted by the liquid sample but instead the intensity thereof is only reduced.

Such a beam can therefore allow the upper portion and the lower portion of the meniscus to be detected, that is to say, the "true" meniscus, but in the case of some samples, the reduction of the intensity of the beam under the effect of air or liquid may be of the same magnitude, so that it is impossible to determine whether the location is above or below the liquid level; such samples cannot consequently be detected.

SUMMARY OF THE INVENTION

The object of the present invention is to provide a device which allows monitoring of the level of the condensate collected in the measuring cylinder of a standard distillation device of the above-mentioned type, which allows these disadvantages to be overcome.

This device comprises an optical system which is capable of transmitting at least one infrared beam which is directed horizontally through the measuring, cylinder and which co-operates with a linear driving action via a step motor which can be moved in vertical translation in order to allow this beam to be aligned with the meniscus of the condensate collected in this cylinder in order to allow the height of this meniscus to be detected.

According to the invention, such a device is characterized in that the optical system comprises:
  on the one hand, a dual optical barrier which is constituted by two transmitter/receiver pairs which are each capable of transmitting a light beam which is directed horizontally through the measuring cylinder and which co-operates with the linear driving action via a step motor in order to allow these beams to be aligned with the meniscus of the condensate collected in this cylinder in order to allow the height of the meniscus to be detected, one of these transmitter/receiver pairs transmitting a first light beam or center beam which is centered on the measuring cylinder in order to allow the lower portion of the meniscus to be detected while the other transmitter/receiver pair transmits a second light beam or eccentric beam which is offset relative to the center beam and which passes between the center and the wall of the measuring cylinder in order to allow the upper portion of the meniscus to be detected, and
  on the other hand, a fixed optical barrier which is constituted by a transmitter/receiver pair which is intended to allow the drops of condensate which fall into the measuring cylinder during distillation to be counted.

The device according to the invention allows the level of the condensate collected in the measuring cylinder of the distillation device to be monitored constantly and in a very precise manner, in so far as, at the beginning of distillation, this monitoring operation can be carried out by means of the eccentric beam which allows the upper portion of the meniscus to be detected while, as soon as possible, it is possible to carry out a commutation in order to carry out this monitoring using the center beam which allows the lower portion of the meniscus to be detected.

During this commutation, it is necessary to take into account the volume of condensate which has fallen into the measuring cylinder during the commutation by carrying out a correction for the number of drops counted by the fixed optical barrier.

The features of the device to which the invention relates will be described in greater detail with reference to the appended drawing which is a schematic plan view of a measuring cylinder co-operating with such a device.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
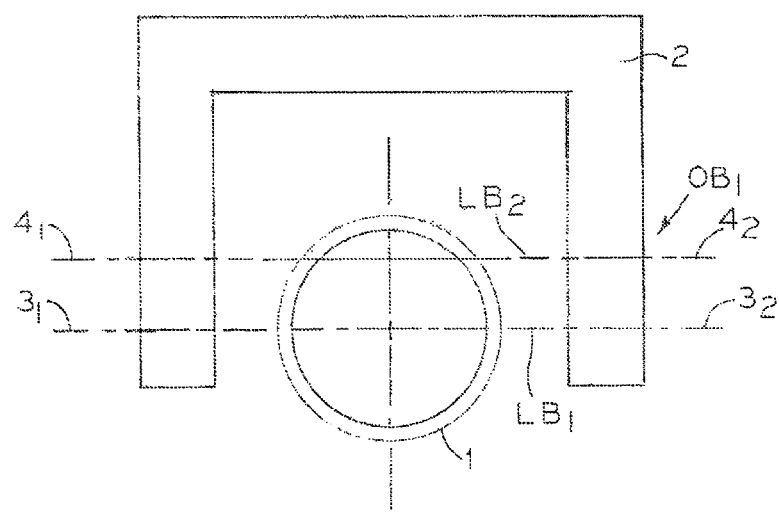
FIG. 1 is a top plan view of a device according to the present invention.

Corresponding reference characters indicate corresponding parts throughout the several views. Although the exemplifications set out herein illustrate an embodiment of the invention, the embodiment disclosed below is not intended to be exhaustive or to be construed as limiting the scope of the invention to the precise form disclosed.

DETAILED DESCRIPTION

Figure 2:
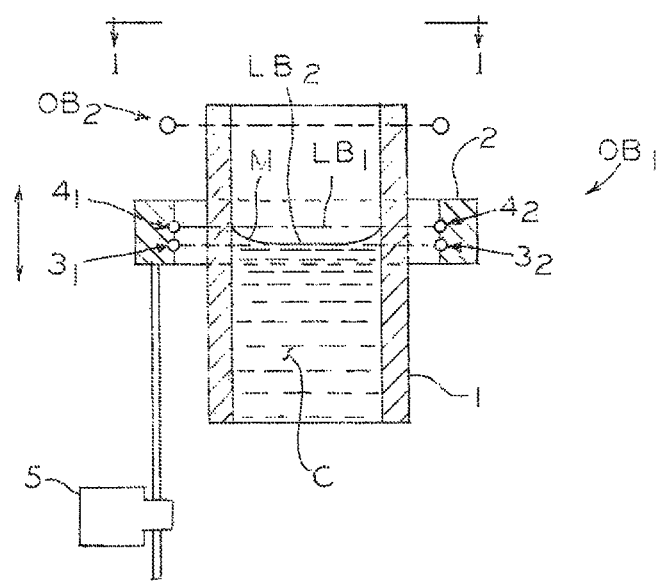
FIG. 2 is a front elevational view the device of FIG. 1.

According to FIGS. 1 and 2, the device comprises a dual optical barrier $OB_1$ which is fixed to a frame 2 which is driven in vertical translation by a linear driving action via a step motor 5 and a fixed optical barrier $OB_2$.

This dual optical barrier $OB_1$ is constituted by two transmitter/receiver pairs $3_1$, $3_2$; $4_1$, $4_2$ which are each capable of transmitting a light beam which is directed horizontally through the measuring cylinder 1.

The light beam $LB_1$ transmitted by the transmitter $3_1$ is a center beam which is centered on the measuring cylinder 1 and allows the receiver $3_2$ to detect the lower portion of the meniscus M of the condensate C collected in this cylinder 1.

The light beam $LB_2$ transmitted by the transmitter $4_1$ is an eccentric beam which is offset relative to the center beam $LB_1$ and which passes between the center and the wall of the measuring cylinder 1; it allows the detector $4_2$ to detect the lower portion of the meniscus M of the condensate C collected in this cylinder 1.

The present invention also relates to a method implemented by the use of the above-mentioned device.

According to this method, the volume V of condensate collected in the measuring cylinder is constantly determined from the height of the lower portion of the meniscus using the equation:

$$V = mX + b \qquad (I)$$

where m and b are parameters corresponding to the gradient and displacement, respectively, at the origin of the calibration line of the distillation device while X represents the distance expressed as steps of linear driving via a step motor between a low reference position corresponding to the base of the measuring cylinder and the height of the lower portion of the meniscus.

The main advantage or this method is connected to the fact that it constantly allows the "true" position of the lower portion of the meniscus to be measured relative to a reference position when, in particular at the beginning of distillation, this lower portion is undetectable taking into account the fact that there is insufficient condensate in the measuring cylinder.

The method according to the invention thus provides similar volume information to that which could be read by the user of a manual distillation device on a calibrated scale etched on the measuring cylinder of this device, but clearly more precise and reliable.

This method is characterized by the succession of the following steps:
  in a preliminary calibration step, the parameters m and b of the equation (I) and the height MH of the meniscus are determined,
  the dual optical barrier is positioned in the low reference position, the step motor is actuated in order to move the dual optical barrier upwards so that the eccentric beam detects and monitors the upper portion of the meniscus, the volume V of condensate collected in the measuring cylinder is calculated using the equation:

$$V = mY + b - MH \quad (II)$$

where Y represents the distance expressed as steps of linear driving via a step motor between the low reference position and the height of the upper portion of the meniscus, this monitoring of the upper portion of the meniscus is continued and the volume V is calculated in accordance with the equation (II) until the center beam can detect the lower portion of the meniscus, the detection is commutated in order to monitor the lower portion of the meniscus using the center beam, and the volume V of condensate collected in the measuring cylinder is calculated using the equation $$V = mX + b \quad (I)$$

with the necessary correction being carried out in order to take into account the volume of condensate collected in the measuring cylinder during the commutation.

According to this method, the height of the upper portion of the meniscus is determined from the position for which the eccentric beam is no longer interrupted by the sample or the meniscus during the upward movement of the linear driving via a step motor.

The commutation itself can be carried out from the time at which the center beam is interrupted by the meniscus for the first time.

Of course, it is generally necessary to carry out several tests in order to attempt to detect the lower portion of the meniscus with the center beam before being able to determine this time.

The method according to the invention further has the advantage of not being disrupted by fumes which may appear in the measuring cylinder during distillation in so far as the lower portion of the meniscus is measured when the center beam is still located below the surface of the liquid sample.

According to another feature of the invention, during the preliminary calibration step, at least two known volumes of sample V1 and V2 are successively introduced into the measuring cylinder and the corresponding distances X1, X2, Y1 and Y2 are measured.

According to the invention, it is by way of example advantageous to successively introduce volumes of 5 ml and 95 ml of sample during the preliminary calibration step.

In the context of this example, the equation I can therefore be written in the following manner:

$$5 \text{ ml} = mX_5 + b$$

$$95 \text{ ml} = mX_{95} + b$$

and by subtraction $$90 \text{ ml} = m(X_{95} - X_5)$$

or $$m = 5 \text{ ml} - \frac{90 \text{ ml}}{X_{95} - X_5}$$

consequently $$b = 5 \text{ ml} - \frac{90 \text{ ml}}{X_{95} - X_5} \cdot X_5$$

The height of the meniscus may also be readily calculated from the difference between the heights $Y_5$ and $X_5$ or $Y_{95}$ and $X_{95}$ and has on average the following value:

$$MH = \frac{(Y_5 - X_5) + (Y_{95} - X_{95})}{2}$$

The values of the parameters m and b and the height MH of the meniscus determined in this manner during the preliminary calibration step can be stored in the memory and constantly used by the automatic distillation device during distillation in order to allow this device to provide the distillation parameters and in particular the quantity of condensate collected as a function of time.

According to another feature of the method according to the invention, during the step for monitoring the upper portion of the meniscus, the volume of the drops of condensate falling into the measuring cylinder is calculated using the fixed optical barrier and, during the commutation step, the necessary correction is carried out for the number of drops of condensate collected during this step and the volume calculated in this manner.

The implementation of such a correction is necessary in order to obtain distillation parameters which are representative in so far as the distillation process is an uninterrupted process and the volume of condensate collected in the measuring cylinder increases constantly during the commutation step between monitoring the upper portion of the meniscus using the eccentric beam and monitoring the lower portion of the meniscus using the center beam.

It is therefore necessary to take this variation into account.

To this end, and by way of example, it is possible to envisage counting using the fixed optical barrier at the beginning of any distillation operation, the number of drops of condensate falling between the time at which the measuring cylinder contains three milliliters of condensate and the time at which the measuring cylinder contains four milliliters of condensate then to derive therefrom by division the volume of a drop.

The volume thus calculated can be used in order to carry out the correction required during the commutation step for the number of drops of condensate falling into the measuring cylinder during this step, as counted again by the fixed optical barrier.

The method according to the invention thus allows constant, reliable and precise monitoring of the level of condensate in the measuring cylinder, and therefore allows distillation parameters to be obtained which are completely representative of the sample to be analyzed.

It should be noted that, during distillation, the condensate may become too opaque to allow the lower portion of the meniscus to be detected.

In this instance, it is possible according to the invention to carry out another commutation in order to monitor again the upper portion of the meniscus by again carrying out the necessary correction in order to take into account the drops of condensate which have fallen into the measuring cylinder during this commutation.

The invention claimed is:

1. A device for use in monitoring a level of condensate collected in a measuring cylinder of a distillation device for distilling liquid samples, comprising:

an optical system, comprising:
a first, dual optical barrier including first and second transmitter/receiver pairs each capable of transmitting a light beam, the light beams respectively directed horizontally through the measuring cylinder with the first and second transmitter/receiver pairs movable via a step motor to align the light beams with a meniscus of the condensate collected in the cylinder, the first transmitter/receiver pair transmitting a first, center light beam which is centered on the measuring cylinder and alignable with a lower portion of the meniscus and the second transmitter/receiver pair transmitting a second, eccentric light beam which is offset relative to the first, center light beam and which passes between the center and the wall of the measuring cylinder and is alignable with an upper portion of the meniscus; and
a second optical barrier including a third transmitter/receiver pair operable to detect and count drops of condensate which fall into the measuring cylinder.

2. A method, implementable by the device of claim 1, for determining a volume V of condensate collected in the measuring cylinder from the height of the lower portion of the meniscus using the equation:

$$V = mX + b \qquad (I)$$

where m and b are parameters corresponding to a gradient and displacement, respectively, at an origin of a calibration line of the distillation device, X is a distance expressed as steps of linear driving via the step motor between a low reference position corresponding to the base of the measuring cylinder and the height of the lower portion of the meniscus, comprising the following steps:
determining, in a preliminary calibration step, the parameters m and b of equation (I) to establish the calibration line of the distillation device and establish a height MH of the meniscus;
positioning the first optical barrier in the low reference position;
actuating the step motor to move the first optical barrier upward to allow the second, eccentric beam to detect and monitor a height of the upper portion of the meniscus;
calculating a volume V of condensate collected in the measuring cylinder using the equation:

$$V = mY + b - MH \qquad (II)$$

where Y represents a distance expressed as steps of linear driving via the step motor between the low reference position and the height of the upper portion of the meniscus;
monitoring the height of the upper portion of the meniscus and calculating the volume V in accordance with the equation (II) until the first, center beam detects the lower portion of the meniscus;
commutating the detection to monitor the lower portion of the meniscus using the first, center beam; and
calculating the volume V of condensate collected in the measuring cylinder using equation I with a correction corresponding to it volume of condensate collected in the measuring cylinder during said commutating step.

3. The method of claim 2, further comprising the following additional steps:
introducing, during said determining step, at least two known volumes of sample V1 and V2 successively into the measuring cylinder; and
measuring corresponding distances X1, X2, Y1 and Y2.

4. The method of claim 2, wherein:
said step of monitoring the height of the upper portion of the meniscus further comprises calculating an initial volume of drops of condensate falling into the measuring cylinder using the second optical barrier; and
said commutating and calculating steps further comprise calculating the volume V using the calculated initial volume.

5. The method of claim 2, further comprising the additional step of:
monitoring the upper portion of the meniscus in the event the condensate becomes too opaque to detect the lower portion of the meniscus.

* * * * *